United States Patent
Hahm et al.

(10) Patent No.: US 11,186,631 B2
(45) Date of Patent: Nov. 30, 2021

(54) ANTI-STAT3 BISPECIFIC ANTIBODY HAVING CELL-PENETRATING ABILITY, AND PHARMACEUTICAL COMPOSITION CONTAINING SAME

(71) Applicant: ROPHIBIO, INC., Cheongju-si (KR)

(72) Inventors: SungHo Hahm, Cheongju-si (KR); JinTae Hong, Cheongju-si (KR)

(73) Assignee: ROPHTBIO, INC., Cheongju-si (KR)

( * ) Notice: Subject to any disclaimer, the term of this patent is extended or adjusted under 35 U.S.C. 154(b) by 0 days.

(21) Appl. No.: 16/907,485

(22) Filed: Jun. 22, 2020

(65) Prior Publication Data
US 2020/0369756 A1 Nov. 26, 2020

Related U.S. Application Data

(63) Continuation of application No. PCT/KR2018/016432, filed on Dec. 21, 2018.

(30) Foreign Application Priority Data

Dec. 22, 2017 (KR) .................. 10-2017-0178028
Dec. 22, 2017 (KR) .................. 10-2017-0178039
Dec. 22, 2017 (KR) .................. 10-2017-0178053
Dec. 22, 2017 (KR) .................. 10-2017-0178084

(51) Int. Cl.
*C07K 16/18* (2006.01)
*C07K 16/44* (2006.01)
*G01N 33/68* (2006.01)

(52) U.S. Cl.
CPC .............. *C07K 16/18* (2013.01); *C07K 16/44* (2013.01); *G01N 33/68* (2013.01); *C07K 2317/31* (2013.01); *C07K 2317/565* (2013.01); *C07K 2317/622* (2013.01); *C07K 2317/76* (2013.01); *C07K 2317/77* (2013.01); *C07K 2317/92* (2013.01)

(58) Field of Classification Search
CPC .... C07K 16/18; C07K 16/44; C07K 2317/76; C07K 2317/77; C07K 2317/622; C07K 2317/31; A61P 35/00; A61P 29/00; A61K 38/00; A61K 48/00; A61K 2039/505; G01N 33/68
See application file for complete search history.

(56) References Cited

U.S. PATENT DOCUMENTS

| | | | | |
|---|---|---|---|---|
| 10,383,945 | B2 * | 8/2019 | Weisbart | C07K 16/44 |
| 2016/0115248 | A1 | 4/2016 | Singh | |
| 2017/0306048 | A1 | 10/2017 | Zhou et al. | |
| 2018/0127509 | A1 * | 5/2018 | Armstrong | C07K 16/30 |
| 2018/0230237 | A1 * | 8/2018 | Herrmann | C07K 16/18 |

FOREIGN PATENT DOCUMENTS

| | | |
|---|---|---|
| KR | 1020090092201 A | 8/2009 |
| KR | 1020160050051 A | 5/2016 |

OTHER PUBLICATIONS

Weisbart RH et al., (2012), "A cell-penetrating bispecific antibody for therapeutic regulation of intracellular targets", Mol. Can. Ther., 11(10):2169-73. (Year: 2012).*
Calo V, et al. (2003) STAT proteins: from normal control of cellular events to tumorigenesis. J Cell Physiol 197(2): 157-168 (Year: 2003).*
Goicochea NL et al., (2017), "Development of cell-penetrating bispecific antibodies targeting the N-terminal domain of androgen receptor for prostate cancer therapy", PEDS, 30(12):785-793 (Year: 2017).*
International Search Report of PCT/KR2018/016432 dated Apr. 2, 2019.
Goicochea, N.L., et al., "Development of Cell-penetrating Bispecific Antibodies Targeting the N-terminal Domain of Androgen Receptor for Prostate Cancer Therapy," Article in Protein Engineering, Design & Selection, Dec. 1, 2017, vol. 30, No. 12, pp. 785-793, (original article inner pp. 1-9).
Sailan Zou, et al., "Targeting STAT3 in Cancer Immunotherapy", Molecular Cancer, Sep. 24, 2020, vol. 19, No. 145, China.
Tammy Bowman, et. al., "STATs in oncogenesis", Oncogene, May 2020, vol. 19, pp. 2474-2488, Tampa, Florida.
Sundas Arshad, et al., "Targeting STAT-3 signaling pathway in cancer for development of novel drugs: Advancements and challenges", Genetics and Molecular Biology, Feb. 2020, Sociedade Brasileira de Genética, Pakistan.
Ruei-Min Lu, et al., "Development of therapeutic antibodies for the treatment of diseases", Journal of Biomedical Science, Jan. 2020, vol. 27, Taipei, Taiwan.

(Continued)

*Primary Examiner* — Sharon X Wen
*Assistant Examiner* — Peter Johansen
(74) *Attorney, Agent, or Firm* — Dinsmore & Shohl LLP; Yongsok Choi, Esq.

(57) ABSTRACT

An anti-STAT3 specific antibody and a pharmaceutical composition comprising the same is provided. The anti-STAT3 specific antibody includes a site that specifically binds to STAT3, and further includes a STAT3 site plus a DNA binding site that confer cell penetration ability, and the pharmaceutical composition includes the anti-STAT3 specific antibody as an active ingredient. The STAT3 specific antibody, and particularly the STAT3/DNA dual specific antibody having a dual specific characteristic, contains a DNA binding site that can penetrate cells and specifically bind to DNA in the nucleus, and thus can overcome the limitations of conventional antibody therapeutics that can target only extracellular proteins. The antibody can inhibit transcription factor activity of STAT3 by specifically binding to phosphorylated activated form of STAT3. Thus, the antibody could be used for the development of a therapeutic agent without side effects for various diseases caused by activation of STAT3.

11 Claims, 3 Drawing Sheets
Specification includes a Sequence Listing.

(56) References Cited

OTHER PUBLICATIONS

Mohammad Zahid Kamran, et al., "Role of STAT3 in Cancer Metastasis and Translational Advances", BioMed Research International, Oct. 2, 2013, vol. 2013, pp. 1-15, Gude lab, Advanced Centre for Treatment, Research & Education in Cancer (ACTREC), Tata Memorial Centre, Kharghar, Navi Mumbai 410210, India.

James E. Hansen, et al., "Intranuclear Protein Transduction through a Nucleoside Salvage Pathway", Journal of Biological Chemistry, Jul. 20, 2007, vol. 282, No. 29, pp. 20790-20793, Veterans Affairs Greater Los Angeles Healthcare System (VAGLAHS), Sepulveda, California 91343, USA.

Suyun Huang, "Regulation of Metastases by Signal Transducer and Activator of Transcription 3 Signaling Pathway: Clinical Implications", Clinical cancer research : an official journal of the American Association for Cancer Research, Mar. 1, 2007, vol. 13, No. 5, pp. 1362-1366, Department of Neurosurgery, The University of Texas M. D. Anderson Cancer Center, Program in Cancer Biology, The University of Texas Graduate School of Biomedical Sciences at Houston, Houston, Texas, USA.

Guilian Niu, et al., "Gene Therapy with Dominant-negative Stat3 Suppresses Growth of the Murine Melanoma B16 Tumor in Vivo", Journal of Cancer Research, Oct. 15, 1999, vol. 59, No. 20, pp. 5059-5063, Moffitt Cancer Center and Research Institute, and Department of Microbiology and Immunology, University of South Florida College of Medicine, Tampa, Florida USA.

\* cited by examiner

FIG. 1A

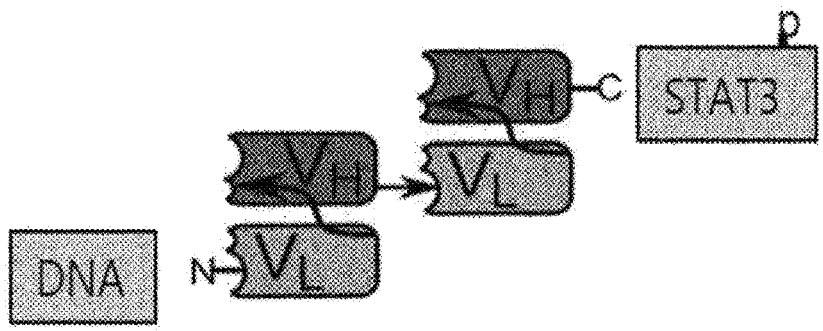

FIG. 1B

STAT3–C4 subtype:
Signal Peptide region
mAB 3E10 Vk(III)

mAB 3E10 Vh
myc mAB PAb421 Vk (KD=4nm; ID=C4)

mAB PAb421 Vh (KD=4nm; ID=C4)
His6 tag

MGFSRIFLFLLSVTTGVHSDIVLTQSPASLAVSLGQRATISCRASKSVSTSSYSYMHWYQQK
PGQPPKLLIKYASYLESGVPARFSGSGSGTDFTLNIHPVEEEDAATYYCQQSREFPWTFGGG
TKLELK̲̲̲̲̲̲̲̲̲̲̲̲̲̲̲̲̲̲̲̲̲̲̲̲̲̲̲EVQLVESGGGLVKPGGSRKLSCAASGFTFSDYGMHWVRQAP
EKGLEWVAYISSGSSTIYYADTVKGRFTISRDNAKNTLFLQMTSLRSEDTAMYYCARRGLLL
DYWGQGTTLTVSSEQKLISEEDLAKTTAPSVYPLAPVLESSGSGQSVLTQPPSASGTPGQRV
TISCSGSSSNIGSNRVSWYQQLPGTAPKLLIYSNNQRPSGVPDRFSGSKSGTSASLAISGLR
SEDEADYYCASWDYSLNAYVFGGGTKLTVLGQAGGGGSGGGGSGGGGSEVQLLESGGGLVQP
GGSLRLSCAVSGFTFSSYMSWVRQAPGKGLEWVSLISPGSGSIYYADSVKGRFTISRDNSK
NTLYLQMNSLRAEDTAVYYCARDLTSQLPDGFDYWGQGTLVTVSSHHHHHH*

FIG. 2

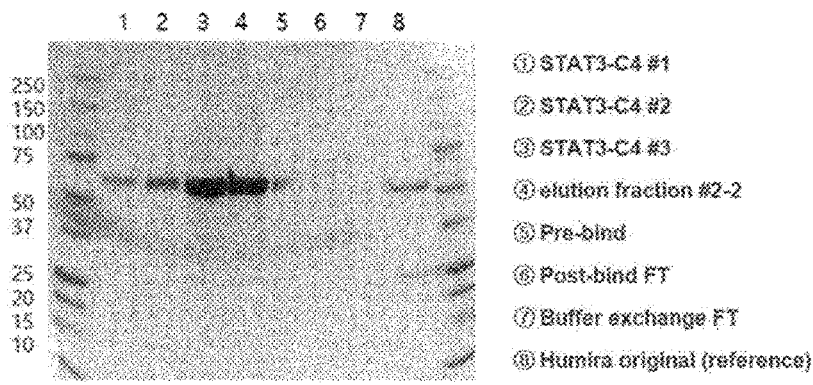

① STAT3-C4 #1
② STAT3-C4 #2
③ STAT3-C4 #3
④ elution fraction #2-2
⑤ Pre-bind
⑥ Post-bind FT
⑦ Buffer exchange FT
⑧ Humira original (reference)

IL-6 mediated gene expression from STAT-RE

ANTI-STAT3 BISPECIFIC ANTIBODY HAVING CELL-PENETRATING ABILITY, AND PHARMACEUTICAL COMPOSITION CONTAINING SAME

CROSS-REFERENCE TO RELATED APPLICATION

This application is a continuation of International Application No. PCT/KR2018/016432 filed on Dec. 21, 2018, which claims priority to Korean Patent Application No. 10-2017-0178028 filed on Dec. 22, 2017, Korean Patent Application No. 10-2017-0178039 filed on Dec. 22, 2017, Korean Patent Application No. 10-2017-0178053 filed on Dec. 22, 2017, Korean Patent Application No. 10-2017-0178084 filed on Dec. 22, 2017, the entire contents of which are herein incorporated by reference.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created Jun. 19, 2020, is named "Sequence Listing PCT" and is 10 kB in size.

BACKGROUND

Field of the Invention

The present invention relates to an anti-STAT3 bispecific antibody having a cell-penetrating ability and a pharmaceutical composition comprising the same, more specifically, an anti-body comprising a site specifically binding to STAT3 and a DNA binding site conferring the cell-penetrating and pharmaceutical compositions comprising it as an active ingredient.

Discussion of Related Art

Proteins are made from genetic information on DNA through transcription and translation processes. The protein produced is a component of the cell and performs functions such as cell skeleton formation, but many proteins have activity, and regulation of protein activity plays a very important role in cell signal transmission for regulation of intracellular function.

Regulation of intracellular signal transduction by proteins can be achieved through on/off of protein activity, and various modification methods such as phosphorylation, glycosylation, methylation, and acetylation, and protein-protein interaction are used for the induction of protein activation or inactivation. As such, post-translational modification plays a very important role in intracellular signal transduction, and among them, protein phosphorylation is a signal derived from the environment outside and inside the cell as the main mechanism of action affecting gene expression (Manning G, et al., the protein kinase complement of the human genome. Science 298: 1912-1934 (2002)).

It is known that such protein phosphorylation is responsible for intracellular signaling by affecting protein activity, structure, and binding ability with other proteins. As molecular biological knowledge develops, new drugs based on this mechanism are being developed. A typical method is to inhibit the activity of proteins that bind to the phosphorylated site of these proteins.

STAT3 (signal transducers and activators of transcription 3), a signaling protein that can induce cell proliferation, when it gets phosphorylated in response to extracellular signals such as interleukin (IL) or interferon-gamma (IFN-γ), gets paired (homo-dimer or hetero-dimer formation) and moves into the nucleus to induce the expression of specific genes. In particular, STAT3 has received a lot of attention as it is known as a cancer-causing factor, and in fact, abnormal activation of STAT3 has been reported in various cancer tissues. In particular, hyperactivated STAT3 is known to promote cancer cellization of mutated cells by promoting expression of target genes such as Bcl-XL, c-myc, and cyclin D1, which are associated with cancer cell survival, proliferation and growth. However, the development of drugs that can effectively suppress STAT3 is still insufficient.

On the other hand, inflammatory disease refers to a disease in which an inflammatory reaction is a major lesion, and among these, rheumatoid arthritis is a chronic inflammatory disease of unknown cause characterized by multiple arthritis. Initially, the synovial membrane surrounding the joints is inflamed, but the inflammation gradually spreads to the surrounding cartilage and bones, leading to destruction and deformation of the joints to become a disease that can invade the whole body, with symptoms outside of the joint, including anemia, dry syndrome, subcutaneous nodules, pulmonary fibrosis, vasculitis, and skin ulcers.

The exact cause of rheumatoid arthritis has not been determined, but autoimmunity is a major mechanism. Autoimmune is an abnormality of the immune system that protects the human body from the outside, rather it attacks the human body. In general, genetic predisposition, bacterial or viral infection, etc. are thought to be the cause of rheumatoid arthritis, and are known to be easy to develop after physical or mental stress. In addition, it has been reported that the incidence is high even in the early stages of menopause, which is an example of rheumatoid arthritis being affected by hormones.

A treatment strategy associated with immunopathological mechanisms is known as a treatment method for rheumatoid arthritis, and several biotherapies are used, but there is no effective clinically sustainable treatment.

On the other hand, until recently, various studies have reported that STAT3 (signal transducers and activators of transcription 3) plays a role as another important transcription factor in addition to NF-κB in autoimmune diseases including rheumatoid arthritis. In particular, it is well known that STAT3 is activated by interleukin-6 (IL-6), a cytokine that mediates an inflammatory response, and thus, and it has been reported continuously activated STAT3 is closely related to the development of rheumatoid arthritis (Rheumatology (Oxford). 2015 June; 54(6):1103-13).

Antibodies are glycoproteins present in serum or tissue fluids of all mammals, and recognize foreign antigens in vivo. Antibodies activate effector functions such as phagocytic ability of FcR expressing cells, antibody-dependent cellular injury ability, mediator freeing ability and antigen presentation ability through activation of the complement system or binding to a receptor (FcR) present on the cell surface, and are involved in biological defense. Based on the antigen-specific binding capacity of these antibodies, various medicines are being developed in the form of recombinant antibodies that bind to substances that cause diseases in cells and inhibit their activity, and they are proved to be an effective drug form as they are easier to produce than other types of drugs, such as low-molecular-weight drugs, with specificity and bio-durability.

Antibodies are glycoproteins found in the blood or tissue fluid of mammalian species, and recognize foreign antigens. Antibodies activate complementary systems, and through the biding to the cell surface receptors (FcR) activate FcR expressing cells' effector functions such as increasing their cell identification capability, antibody-dependent cell mediated cytotoxicity, mediators release, and antigen presentation capability, and protect the body.

However, while typical antibodies can only target extracellular molecules, numerous important targets for the treatment of diseases and diagnosis of diseases are located inside the cells. For example, many transcription factors, especially STAT3, are recognized as the most important but challenging targets for the treatment of various diseases.

Thus, the present invention has developed an antibody capable of penetrating into cells targeting only the activated STAT3, thereby solving the above-described conventional limitations, and treating cancer, suppressing cancer metastasis, and using it for treating STAT3-related diseases.

Accordingly, the present invention has developed an antibody capable of penetrating into cells targeting only the activated STAT3, thereby solving the above-described conventional limitations, and treating cancer, suppressing cancer metastasis, and treating STAT3-related diseases.

SUMMARY

Technical Problem

The present invention has been devised to overcome the above-described conventional limitations, and the present inventors completed the invention by developing a STAT3 specific antibody with its first antigen-binding site specifically binding to phosphorylated STAT3, and an antibody with cell penetrating ability and bispecific property that specifically binds to phosphorylated STAT3 and intracellular DNA.

Accordingly, an object of the present invention is to provide a STAT3 specific antibody or fragment thereof, comprising a first antigen binding site that specifically binds to STAT3 (Signal transducer and activator of transcription 3). In addition, the purpose is to provide a STAT3 specific antibody or fragment, with the STAT3 specific antibody or fragment thereof further includes a separate second antigen binding site that specifically binds to DNA, and so with STAT3/DNA dual specific properties.

Another object of the present invention is to provide a polynucleotide encoding the antibody or fragment thereof, a vector containing the polynucleotide, and a cell transformed with the vector.

In addition, another object of the present invention is to provide a method for producing the above-mentioned antibody or a fragment thereof, and a method for specifically detecting them.

In addition, an object of the present invention is to provide a pharmaceutical composition for the treatment of cancer, comprising an STAT3/DNA bispecific antibody or a fragment thereof as an active ingredient.

In addition, it is an object of the present invention to provide a pharmaceutical composition for inhibiting cancer metastasis, comprising a STAT3/DNA bispecific antibody or a fragment thereof as an active ingredient.

In addition, an object of the present invention is to provide a pharmaceutical composition for the treatment of inflammatory diseases, comprising an STAT3/DNA bispecific antibody or a fragment thereof as an active ingredient.

However, the intention of the present invention is not limited to the above-mentioned objects, and other objects not mentioned above can become more fully understood from the following description.

Technical Solution

In order to achieve the object of the present invention as described above, the present invention provides a STAT3 specific antibody or fragment thereof comprising a first antigen binding site that specifically binds to STAT3 (Signal transducer and activator of transcription 3).

In one embodiment of the present invention, the antibody or fragment thereof may further have a STAT3/DNA dual specific property, further comprising a second antigen binding site that specifically binds to DNA.

In one embodiment of the present invention, the first antigen binding site specific for STAT3 may contain a light chain complementarity determining region (CDR) represented by the amino acid sequence of SEQ ID NOs: 1 to 3, and a heavy chain complementarity determining region represented by the amino acid sequence of SEQ ID NOs: 4 to 6.

In another embodiment of the present invention, the first antigen-binding site specifically binding to STAT3 may contain a light chain complementarity determining region (CDR) represented by the amino acid sequence of SEQ ID NOs: 7 to 9, and a heavy chain complementarity determining region represented by the amino acid sequence of SEQ ID NOs: 10 to 12.

In another embodiment of the present invention, the first antigen-binding site specifically binding to STAT3 comprises a light chain complementarity determining region (CDR) represented by the amino acid sequence of sequence ID Nos: 13 to 15, and a heavy chain complementarity determining region represented by the amino acid sequence of SEQ ID NOs: 16 to 18.

In one embodiment of the present invention, the first antigen binding site specific for STAT3 may contain a light chain complementarity determining region (CDR) represented by the amino acid sequence of SEQ ID NOs: 19 to 21, and a heavy chain complementarity determining region represented by the amino acid sequence of SEQ ID NOs: 22 to 24.

In one embodiment of the present invention, the first antigen binding site specific for STAT3 may contain a light chain complementarity determining region (CDR) represented by the amino acid sequence of SEQ ID NOs: 25 to 27, and a heavy chain complementarity determining region represented by the amino acid sequence of SEQ ID NOs: 28 to 30.

In one embodiment of the present invention, the first antigen binding site specific for STAT3 may contain a light chain complementarity determining region (CDR) represented by the amino acid sequence of SEQ ID NOs: 31 to 33, and a heavy chain complementarity determining region represented by the amino acid sequence of SEQ ID NOs: 34 to 36.

In one embodiment of the present invention, the first antigen binding site specific for STAT3 may contain a light chain complementarity determining region (CDR) represented by the amino acid sequence of SEQ ID NOs: 37 to 39, and a heavy chain complementarity determining region represented by the amino acid sequence of SEQ ID NOs: 40 to 42.

In another embodiment of the present invention, the STAT3 may be with a phosphorylated 705th tyrosine residue.

In another embodiment of the present invention, the antibody or fragment thereof may have an ability to penetrate into cells.

In another embodiment of the present invention, the above-mentioned fragments can be a fragment selected from diabody, Fab, Fab', F(ab)2, F(ab')2, Fv, and scFv.

In addition, the present invention provides a polynucleotide encoding the above antibody or fragment thereof.

In addition, the present invention provides a vector comprising the above polynucleotide.

In addition, the present invention provides cells transformed with the above-mentioned vector.

In addition, the present invention provides methods for the production of STAT3 specific antibody or fragment thereof including steps for (a) culturing the above-mentioned cells under the conditions that allow expression of the polynucleotide;

(b) producing polypeptides comprising sites for the light chain CDR and heavy chain CDR from the above cells;

(c) recovering the above polypeptides either from the cells or from their culture medium.

In addition, the present invention provides a method for specific detection of STAT3, comprising contacting the antibody or fragment thereof with a sample and detecting the antibody or fragment thereof.

In addition, the present invention provides a pharmaceutical composition for treating cancer, comprising a STAT3 specific antibody or a fragment thereof as an active ingredient.

In addition, the present invention provides a pharmaceutical composition for inhibiting cancer metastasis, comprising a STAT3 specific antibody or a fragment thereof as an active ingredient.

In one embodiment of the present invention, the cancer can be one or more selected from bladder cancer, breast cancer, cervical cancer, cholangiocarcinoma, colorectal cancer, colon cancer, endometrial cancer, esophageal cancer, stomach cancer, head and neck cancer, kidney cancer, liver cancer, lung cancer, nasopharyngeal cancer, ovarian cancer, pancreatic cancer, gallbladder cancer, prostate cancer, thyroid cancer, osteosarcoma, rhabdomyosarcoma, lubricating sarcoma, Kaposi's sarcoma, smooth sarcoma, malignant fibrosarcoma, fibrosarcoma, acute myeloid leukemia, adult T cell leukemia, chronic myelogenous leukemia, lymphoma, multiple myeloma, glioblastoma, astrocytoma, melanoma, mesothelioma, Wilm's tumor, and MiT tumors including clear cell sarcoma (CCS), afferent soft sarcoma (ASPS) and translocation-associated renal cell carcinoma.

In addition, the present invention provides a method of treating cancer, comprising administering the pharmaceutical composition to an individual.

In addition, the present invention provides a cancer treatment of the pharmaceutical composition.

In addition, the present invention provides a method for inhibiting cancer metastasis, comprising administering the pharmaceutical composition to an individual.

In addition, the present invention provides the use of the pharmaceutical composition for inhibiting cancer metastasis.

In addition, the present invention provides a pharmaceutical composition for the treatment of inflammatory diseases, comprising an STATS/DNA bispecific antibody or fragment thereof as an active ingredient.

In one embodiment of the invention, the inflammatory disease may be rheumatoid arthritis (rheumatoid arthritis) or psoriasis dermatitis (psoriasis).

In addition, the present invention provides a method of treating an inflammatory disease, comprising administering the pharmaceutical composition to an individual.

In addition, the present invention provides a pharmaceutical composition for the treatment of inflammatory diseases.

Advantageous Effects

The STAT3 specific antibody according to the present invention can specifically inhibit only its phosphorylation activated form of STAT3, thereby inhibiting its transcription factor activity. In addition, the STAT3 specific antibody according to the present invention may further include a second antigen binding site that specifically binds to DNA, and may have STAT3/DNA dual specific properties.

In particular, antibodies with dual STAT3/DNA specific characteristics can overcome the limitations of antibody drugs targeting only proteins existing outside cells, by including a DNA binding site that penetrates into cells and specifically binds to DNA in the nucleus. In addition, it was confirmed that it is capable of inhibiting its transcription factor activity by specifically binding to phosphorylation activated form of STAT3, and thus they can used effectively for the development of a therapeutic agent without side effects for related diseases caused by activation of STAT3, for example, development of a therapeutic agent for various carcinomas related to STAT3 activation, development of a drug capable of inhibiting cancer metastasis progressed by activation of STAT3, and a therapeutic agent without side effects for inflammatory diseases including rheumatoid arthritis and psoriatic dermatitis associated with activation of STAT3.

BRIEF DESCRIPTION OF THE DRAWINGS

FIG. 1a briefly shows the structure of an antibody (hereinafter referred to as pSTAT3 antibody) specifically binding to phosphorylated STAT3.

FIG. 1b shows the antibody structure of the present invention and its sequence.

FIG. 2 shows a result of confirming the ability to bind to phosphorylated STAT3 by performing SDS-PAGE after producing an antibody having the pSTAT3 dual specific characteristics of the present invention.

DETAILED DESCRIPTION

Figure 3:
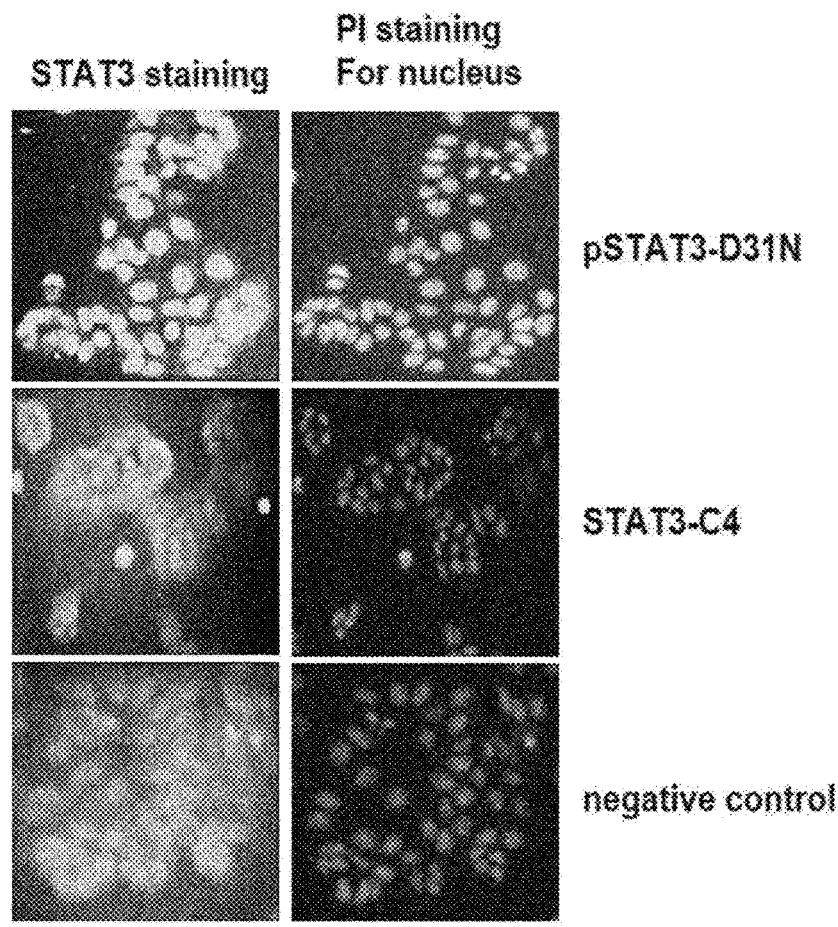
FIG. 3 is a result of confirming the cell penetration ability of the antibody having the pSTAT3 dual specific properties of the present invention through immunocytochemical staining.

The present inventors completed the invention by developing an antibody capable of specifically binding to phosphorylated STAT3 and inhibiting its transcription factor activity, and further developing an antibody that specifically binds to intracellular DNA and has a dual specific property with cell penetration ability.

Accordingly, the present invention provides a STAT3 specific antibody or fragment thereof comprising a first antigen binding site that specifically binds to STAT3 (Signal transducer and activator of transcription 3).

In addition, the present invention provides STAT3-specific antibodies or fragments thereof, comprising a first antigen-binding site that specifically binds to STAT3 (Signal transducer and activator of transcription 3) and a second antigen-binding site that specifically binds DNA, thereby STAT3/DNA dual specific properties.

The present inventors prepared the STAT3 specific antibody or fragment thereof through Examples and verified its function.

In one embodiment of the present invention, a total of 24 specific antibody sequences that bind to the pY705 STAT3 peptide antigen were derived using a human single-chain variable fragment (scFv) library using a phage display method, and affinity (KD) was measured. Thus, seven antibody candidates with high affinity for pY705 STAT3 were finally selected (see Example 1).

In another embodiment of the present invention, a recombinant antibody was prepared using 3 sequences among the 7 candidates, and it was confirmed that pSTAT3 can be effectively detected by an antibody produced using one of these sequences by performing SDA-PAGE. (See Example 2).

In another embodiment of the present invention, as a result of verifying the intracellular penetration ability of the antibody through a cell immunochemical staining method in a colon cancer cell line, it was confirmed that the pSTAT3 antibody containing a DNA binding domain has an effective intracellular penetration ability (Example 3).

In another embodiment of the present invention, the mouse macrophage cell line and the articular bone marrow cell were treated with the antibody according to the present invention, and the expression level of pSTAT3 was measured by Western blot to confirm the ability of the antibody to inhibit pSTAT3, but this function had no effect on other signal transduction molecules (see Example 4-1).

In another embodiment of the present invention, it was confirmed that the antibody inhibits the expression of the luciferase reporter gene in IL-6 stimulation conditions using a luciferase reporter gene expressed under the control of STAT3-RE (See Example 4-2).

The results of the above examples demonstrate that the STAT3 specific antibody according to the present invention, and more specifically, the STAT3 specific antibody having the STAT3/DNA dual specific property has cell penetration ability and effectively inhibits the function of pSTAT3. Furthermore, it is to prove that it can be usefully used for treatment of various carcinomas related to activation of STAT3, inhibition of cancer metastasis, and treatment of inflammatory diseases.

The term "antibody" used in the present invention includes immunoglobulin molecules that are immunologically reactive with a specific antigen, and includes both polyclonal antibodies and monoclonal antibodies. In addition, the term includes forms produced by genetic engineering, such as chimeric antibodies (eg, humanized murine antibodies), heterologous antibodies (eg, bispecific antibodies), and bispecific antibodies. In the present invention, the antibody may be an antibody having specific characteristics or dual specific characteristics, and the antibody having the dual specific characteristics means an antibody having two binding sites specific for different antigens of one antibody. As such, the antibody of the present invention can preferably bind to STAT3 or STAT3 and intracellular DNA, respectively.

The terminology "antibody" used in the present invention includes immunoglobulins molecules that specifically interact with antigens, and includes both monoclonal and polyclonal antibodies. Also, the above terminology includes chimeric antibodies (such as humanized murine antibodies) and bispecific antibodies that can be developed by genetically engineering them. Bispecific antibody provided in the present invention refers to an antibody with binding sites for two different antigens, and preferably in the present invention for STAT3 and cellular DNA, respectively.

'Antibody' and 'anti STAT3 specific antibody' of the present invention should be understood to include a binding site that specifically binds to STAT3, and 'STAT3/DNA bispecific antibody' and 'STAT3 bispecific scFv antibody' should be understood that it includes both a binding site that specifically binds STAT3 and a binding site that specifically binds DNA. Meanwhile, the terms "first" and "second" used in the specification of the present invention should be understood to be randomly ordered for classification.

Antibodies typically have heavy and light chains, and each heavy and light chain contains a constant region and a variable region (this region is also known as a "domain"). The variable regions of the light and heavy chains include three variable regions called "complementarity-determining regions" (hereinafter referred to as "CDRs") and four "framework regions". The CDR mainly plays a role of binding to the epitope of the antigen. The CDRs of each chain are typically called CDR1, CDR2, CDR3, starting from the N-terminus, and are also identified by the chain in which the particular CDR is located. However, not all CDR sites need to be directly involved in antigen binding.

In the present invention, the first antigen-binding site specifically binding to STAT3 can be a light chain complementarity determining region (CDR) represented by the amino acid sequence of SEQ ID NOs: 1 to 3 and a heavy chain complementarity determining region represented by the amino acid sequence of SEQ ID NOs: 4 to 6.

In addition, the first antigen-binding site specifically binding to STAT3 is represented by the light chain complementarity determining region (CDR) represented by the amino acid sequence of SEQ ID NOs: 7 to 9 and a heavy chain complementarity determining region represented by the amino acid sequence of SEQ ID NOs: 10 to 12.

In addition, the first antigen-binding site specifically binding to STAT3 is represented by the light chain complementarity determining region (CDR) represented by the amino acid sequence of SEQ ID NOs: 13 to 15 and a heavy chain complementarity determining region represented by the amino acid sequence of SEQ ID NOs: 16 to 18.

In addition, the first antigen-binding site specifically binding to STAT3 is represented by the light chain complementarity determining region (CDR) represented by the amino acid sequence of SEQ ID NOs: 19 to 21 and a heavy chain complementarity determining region represented by the amino acid sequence of SEQ ID NOs: 22 to 24.

In addition, the first antigen-binding site specifically binding to STAT3 is represented by the light chain complementarity determining region (CDR) represented by the amino acid sequence of SEQ ID NOs: 25 to 27 and a heavy chain complementarity determining region represented by the amino acid sequence of SEQ ID NOs: 28 to 30.

In addition, the first antigen-binding site specifically binding to STAT3 is represented by the light chain complementarity determining region (CDR) represented by the amino acid sequence of SEQ ID NOs: 31 to 33 and a heavy chain complementarity determining region represented by the amino acid sequence of SEQ ID NOs: 34 to 36.

In addition, the first antigen-binding site specifically binding to STAT3 is represented by the light chain complementarity determining region (CDR) represented by the amino acid sequence of SEQ ID NOs: 37 to 39 and a heavy chain complementarity determining region represented by the amino acid sequence of SEQ ID NOs: 40 to 42.

The fragment of the present invention may be a fragment selected from the group consisting of diabody, Fab, Fab', F(ab)2, F(ab')2, Fv and scFv, but is not limited thereto.

In the present invention, a fragment of an antibody refers to a fragment of an antibody that maintains the antigen-specific binding ability of the entire antibody, preferably the fragment is at least 20%, 50%, 70%, 80 of STAT3 and DNA affinity of the parent antibody, and specifically, it may be in the form of Fab, F(ab)2, Fab', F(ab')2, Fv, diabody, scFv, and the like.

For the purpose of the present embodiment, the fragment of the antibody is not limited in structure or form as long as it maintains binding specificity to human-derived STAT3 protein and DNA, but may be preferably scFv. The scFv according to the present embodiment has a CDR configuration, specific to the above-described STAT3 protein and DNA, or VH and VL configuration, and the sequence of scFv is not limited if the C-terminal of VH and the N-terminal of VL are linked via a linker. The linker is not limited as long as it is known in the art as a linker applied to scFv.

The antibodies or fragments thereof of the embodiment may comprise conservative amino acid substitutions (referred to as conservative variants of antibodies) that do not substantially alter their biological activity.

The STAT3 is a transcription factor encoded by the STAT3 gene, and when phosphorylated by receptor-associated Janus kinases (JAK) upon stimulation of various cytokines and growth factors, a homodimer or a heterodimer is formed and it acts as a transcription factor that regulates the expression of various genes by moving to the nucleus. When interferon, epidermal growth factor (EGF), interleukin-5 (IL-5), or interleukin-6 (IL-6) is bound as a ligand, phosphorylation at 705th tyrosine residue of STAT3 occurs, and phosphorylation at 727th serine residue occurs by Mitogen-activated protein kinases (MAPK) or c-src nonreceptor tyrosine kinase. It is known that STAT3 activated through this process mediates the expression of various genes in response to cell stimulation and plays an important role in various cell responses such as cell growth and apoptosis.

In the present invention, the STAT3 to which the STAT3 specific antibody or fragment thereof binds is preferably characterized in that the 705th tyrosine residue is phosphorylated.

On the other hand, the second antigen-binding site that specifically binds to the DNA is a DNA binding domain of 3E10, an autoantibody found in patients with lupus (J Autoimmun. 1998 October; 11(5):539-46. 1998.10), specifically, the 31st aspartic acid of 'Variant heavy chain' is substituted with asparagine (D31N), but is not limited thereto.

In addition, the present invention provides a polynucleotide encoding the antibody or fragment thereof.

The term 'polynucleotide' used in the present invention may be described as an oligonucleotide or a nucleic acid, DNA molecules (eg, cDNA or genomic DNA), RNA molecules (eg, mRNA), nucleotide analogs of the DNA or RNA generated using them (eg, peptide nucleic acids and non-naturally occurring nucleotide analogs) and hybrids thereof. The polynucleotide may be single-stranded or double-stranded.

The sequence of the polynucleotide of the present invention is not particularly limited as long as it encodes the antibody or fragment thereof of the present invention.

The polynucleotide encoding the antibody or fragment thereof of the present invention can be obtained by methods well known in the art. For example, they can be synthesized based on a DNA sequence or a corresponding amino acid sequence encoding part or all of the heavy and light chains of the antibody, by oligonucleotide synthesis techniques well known in the art, and such as polymerase chain reaction (PCR).

In addition, the present invention provides a vector comprising the polynucleotide.

The term 'vector' used in the present invention is used for the purpose of the replication or expression of the polynucleotide of the present invention, for the recombinant production of the antibody or fragment thereof of the present invention, and generally comprised the signal sequence, origin of replication, one or more of the marker genes, enhancer elements, promoters, and transcription termination sequences. The vector of the present invention may preferably be an expression vector, and more preferably, a control sequence, for example, a vector comprising the polynucleotide of the present invention operably linked to a promoter.

In addition, the present invention provides cells transformed with the vector.

The cell of the present invention is not particularly limited as long as it can be used to express a polynucleotide encoding an antibody or fragment thereof included in the expression vector of the present invention. Cells (host cells) transformed with an expression vector according to the present invention include prokaryotes (eg, *E. coli*), eukaryotes (eg, yeast or other fungi), plant cells (eg, tobacco or tomato plants). animal cells (e.g., human cells, monkey cells, hamster cells, rat cells, mouse cells, insect cells, or hybridomas derived therefrom), but preferably It may be cells derived from mammals, including humans.

The term 'transformation' used in the present invention refers to a modification of a host cell genotype by introduction of a foreign polynucleotide, and the foreign polynucleotide is introduced into the host cell regardless of the method used for the transformation. Exogenous polynucleotides introduced into a host cell can be maintained integrated or unintegrated into the genome of the host cell, and the present invention includes both.

Recombinant expression vectors capable of expressing a STAT3 specific antibody or fragment thereof according to the present invention, or a STAT3 specific antibody or fragment thereof having STAT3/DNA dual specific properties, can be introduced inside cells to transform them for producing antibodies or fragments thereof by known methods for introducing nucleic acids into cells, but the transformation method is not limited thereto, for example, transient transfection, microinjection, transduction, cell fusion, calcium phosphate precipitation, liposome-mediated transfection, DEAE dextran-mediated transfection (DEAE dextran-mediated transfection). polybrene-mediated transfection, electroporation, gene guns, etc.

In addition, the present invention provides a method for producing a STAT3-specific antibody or fragment thereof in steps of culturing the cells under the conditions in which the polynucleotide is expressed, producing a polypeptide comprising a light chain and a heavy chain variable region, and recovering the polypeptide from the cell or the culture medium in which it was cultured.

The culture of the cells may have different media composition and culture conditions depending on the type of the cells, which can be appropriately selected and controlled by those skilled in the art.

The antibody molecule may be accumulated in the cytoplasm of the cell, secreted from the cell, or targeted to a periplasmic or supernatant by an appropriate signal sequence, and it is preferably targeted to a periplasmic or extracellular medium. In addition, it is preferable to refold the produced antibody molecule using a method well known to those skilled in the art and have a functional conformation. The recovery of the polypeptide may vary depending on the characteristics of the produced polypeptide and the characteristics of the cell, which can be appropriately selected and controlled by those skilled in the art.

In addition, the present invention provides a method for specific detection of STAT3 comprising contacting the antibody or fragment thereof with a sample and detecting the antibody or fragment thereof.

Those skilled in the art can appropriately select a known method for detecting a protein using an antibody, and prepare a sample suitable for the selected method. In addition, the sample may be a cell or tissue, blood, whole blood, serum, plasma, saliva, cerebrospinal fluid, or the like obtained by a biopsy taken from a subject to diagnose cancer or cancer metastasis. The method for detecting a protein using the antibody is not limited thereto, for example, Western blot, immunoblot, dot blot, immunohistochemistry, enzyme immunoassay (ELISA), radioimmunoassay, Competitive binding analysis, and immunoprecipitation.

The antibody or fragment thereof can be generally labeled with a detectable moiety for its 'detection'. For example, it can be labeled with radioactive isotopes or fluorescent labels, various enzyme-substrate labels that are available, and examples of such enzymatic labels are luciferases, luciferin, such as *Drosophila* luciferase and bacterial luciferase, Peroxidase such as 2,3-dihydrophthalazinediones, malate dehydrogenase, urase, horseradish peroxidase (HRPO), alkaline phosphatase, β-galactosidase, Glucoamylase, lysozyme, saccharide oxidase (e.g. glucose oxidase, galactose oxidase, and glucose-6-phosphate dehydrogenase), heterocyclic oxidase (e.g. uricase and xanthine oxidase), Lactoperoxidase, microperoxidase, and the like. Techniques for conjugating an enzyme to an antibody can be conjugated directly or indirectly to the antibody using known techniques. For example, the antibody can be conjugated to biotin and any markers falling within the three broad categories mentioned above can be conjugated with avidin, or vice versa. Biotin selectively binds to avidin, so this label can be conjugated to the antibody in this indirect manner.

On the other hand, the present invention provides a pharmaceutical composition for treating cancer, comprising a STAT3/DNA specific antibody or a fragment thereof as an active ingredient.

In addition, the present invention provides a pharmaceutical composition for inhibiting cancer metastasis, comprising a STAT3/DNA specific antibody or a fragment thereof as an active ingredient.

On the other hand, the disease targeted for treatment in the present invention, "cancer", is a generic term for diseases caused by cells with metastatic properties, with an aggressive characteristic in which cells divide and grow, ignoring normal growth limits, with an invasive characteristic that penetrates surrounding tissues, and other parts of the body.

On the other hand, the term used in the present invention, "cancer metastasis" is a phenomenon that appears as a result of the progression of cancer, most of the causes of cancer are not primary, and is supposed to be caused by a disturbance the function of organs essential for survival. Cancer metastasis occurs through a plurality of processes, such as migration of cells into tissues or vasculatures, including blood vessels such as arteries and veins, or lymphatic vessels, implantation in other organs, proliferation and tumor tissue formation. It is characterized in that an enzyme is expressed on the cell surface that induces destructiveness of structures that maintain the integrity of tissues such as the basement membrane in addition to the extracellular structure that increases mobility, which decreases adhesion between cells of the same type and creates adhesion to other cells in the operation of important cells in this process.

On the other hand, in the present invention, the cancer is bladder cancer, breast cancer, cervical cancer, cholangiocarcinoma, colorectal cancer, colon cancer, endometrial cancer, esophageal cancer, stomach cancer, head and neck cancer, kidney cancer, liver cancer, lung cancer, nasopharyngeal cancer, ovarian cancer, pancreatic cancer, Gallbladder cancer, prostate cancer, thyroid cancer, osteosarcoma, rhabdomyosarcoma, lubricating sarcoma, Kaposi's sarcoma, smooth muscle sarcoma, malignant fibrous histiocytosis, fibrosarcoma, acute myeloid leukemia, adult T cell leukemia, chronic myelogenous leukemia, lymphoma, multiple One or more selected from the group consisting of myeloma, glioblastoma, astrocytoma, melanoma, mesothelioma, Wilm's tumor, and MiT tumors, including clear cell sarcoma (CCS), afferent soft sarcoma (ASPS) and translocation-associated renal cell carcinoma. It may be, but is not limited thereto.

In addition, the present invention provides a pharmaceutical composition for the treatment of inflammatory diseases, comprising a STAT3/DNA specific antibody or a fragment thereof as an active ingredient.

On the other hand, the disease to be treated in the present invention, "inflammatory disease" refers to a disease in which an inflammatory response is a major lesion, and may include various diseases related thereto, but the inflammatory disease in the present invention is preferably rheumatoid arthritis or psoriatic dermatitis.

The rheumatoid arthritis is an inflammatory disease whose cause has not been precisely identified, and the inflammation caused by the synovial membrane that initially surrounds the joint gradually spreads to surrounding cartilage and bones, thereby causing joint destruction and deformation. It has been reported through various studies in the field that STAT3 and its related signaling are involved in the pathogenesis of rheumatoid arthritis.

The pharmaceutical composition according to the present invention includes a STAT3 specific antibody as an active ingredient, and may further include a pharmaceutically acceptable carrier. The pharmaceutically acceptable carrier is commonly used in formulation, and includes, but is not limited to, saline, sterile water, Ringer's solution, buffered saline, cyclodextrin, dextrose solution, maltodextrin solution, glycerol, ethanol, liposomes, etc. If necessary, it may further contain other conventional additives such as antioxidants, buffers, if necessary. In addition, diluents, dispersants, surfactants, binders, lubricants, and the like may be additionally added to formulate into injectable formulations such as aqueous solutions, suspensions, emulsions, pills, capsules, granules or tablets. Regarding suitable pharmaceutically acceptable carriers and formulations, the formulations described in Remington's literature can be used to formulate according to each component. The pharmaceutical composition of the present invention is not particularly limited in the formulation, but may be formulated as an injection, an inhalant, or an external preparation for skin.

The pharmaceutical composition of the present invention may be administered orally or parenterally (eg, intravenously, subcutaneously, intraperitoneally, or topically) according to a desired method, but may preferably be administered orally. Depending on the patient's condition and body weight, the degree of disease, the route and time of administration can be appropriately selected by those skilled in the art.

The pharmaceutical composition of the present invention is administered in a pharmaceutically effective amount. In the present invention, "a pharmaceutically effective amount" refers to an amount sufficient to treat a disease at a ratio of rational benefit/risk applicable to medical treatment, and an effective dose level can be determined based on the patient's disease type, or severity. It can be determined according to the activity of the drug, the sensitivity to the drug, the time of administration, the route of administration and discharge rate, the duration of treatment, the factors including the drugs used simultaneously, and other factors well known in the medical field. The pharmaceutical composition according to the present invention may be administered as an individual therapeutic agent or in combination with other therapeutic agents, and may be administered sequentially or simultaneously with a conventional therapeutic agent, and may be administered in single or multiple doses. Considering all of the above factors, it is important to administer an amount that can achieve the maximum effect in a minimal amount without side effects, which can be easily determined by those skilled in the art Specifically, the effective amount of the pharmaceutical composition of the present invention may vary depending on the patient's age, sex, condition, weight, absorption of active ingredients in the body, inactivation rate and excretion rate, disease type, and drugs used in combination. In general, 0.001 mg to 150 mg per 1 kg of body weight, preferably 0.01 to 100 mg, may be administered daily or every other day or may be administered by divided into 1 to 3 times a day. However, since the dosage may be increased or decreased depending on the route of administration, the severity of obesity, sex, weight, and age, the dosages does not limit the scope of the present invention in any way.

In another aspect of the present invention, the present invention provides a method of treating cancer comprising administering the pharmaceutical composition to an individual.

In another aspect of the present invention, the present invention provides a method for inhibiting cancer metastasis comprising administering the pharmaceutical composition to a subject.

In another aspect of the present invention, the present invention provides a method of treating an inflammatory disease comprising administering the pharmaceutical composition to an individual.

In the present invention, "individual" refers to a subject in need of treatment of a disease, and more specifically, human or non-human primate, mouse, rat, dog, cat, horse, and cow. It means mammal.

As another aspect of the present invention, the present invention provides treatment use of the pharmaceutical composition for a cancer.

As another aspect of the present invention, the present invention provides treatment use of the pharmaceutical composition for a cancer metastasis.

As another aspect of the present invention, the present invention provides treatment use of the pharmaceutical composition for inflammatory diseases.

Hereinafter, preferred embodiments are provided to help understanding of the present invention. However, the following examples are only provided to more easily understand the present invention, and the contents of the present invention are not limited by the following examples Example 1

Phosphorylated STAT3 Peptide Specific Antibody Sequence Identification and Candidate Selection Using Phage Display In order to prepare an antibody that specifically binds to the 705th tyrosine residue phosphorylated STAT3 (pY705 STAT3), the inventors first tried to screen the antibody that binds to the phosphorylated STAT3 using a phage display.

To this end, first, the human single-chain variable fragment (scFv) library provided by the Osong Advanced Complex Development Center candidate antibody discovery support team was used, and phage display was performed using the pY705 STAT3 peptide as an antigen. Specifically, a phage antibody library was mixed with an antigen fixed on a solid surface to induce antibody-antigen binding, and unbound phages were removed (Washing). Next, after eluting the phage binding to the antigen using an alkaline/acidic pH solution or a competitive peptide, etc., amplifying the eluted phage by infecting E. coli and amplifying the phage Used for round panning to concentrate specific antibodies. As a result, finally, 24 pY705 STAT3 peptide specific antibody sequences were derived.

Then, as shown in Table 1 below, among the 24 sequences, KD was lower than 90 nM, and 7 antibody candidates with high affinity for pY705 STAT3 were finally selected, and 3 candidate antibodies with a KD of 4-6 nM (C4, 3A10, and C6) were selected to proceed with the development of a recombinant bispecific antibody.

TABLE 1

| ID | KD (nM) |
|---|---|
| C4 | 4 |
| 3A10 | 5 |
| C6 | 6 |
| H9 | 12 |
| A12 | 55 |
| F11 | 55 |
| A10 | 85 |

Example 2. Production of Phosphorylated STAT3 Specific Recombinant Antibody

The present inventors tried to construct a recombinant bispecific antibody specific for phosphorylated STAT3

(pY705 STAT3) and DNA, using the three candidate sequences finally selected in Example 1.

The dual antibody produced in the present invention has a structure in which the antigen-binding site at one end binds to phosphorylated STAT3 while the other antigen-binding site binds to DNA in the cell's nucleus, as shown in FIG. 1A. More specifically, as shown in FIG. 1B, scFv (STAT3 scFv) that binds to phosphorylated STAT3 and scFv (3E10 scFv) that penetrates into cells and binds to DNA in the nucleus are joined together with a swivel linker. The 3E10 scFv is a DNA binding domain of an autoantibody found in lupus patients, and furthermore, the aspartic acid (shown in blue) residue at the 31' position of the 'variable heavy chain' was substituted into asparagine (D31N), as it has been reported that the penetration efficiency in cells is further improved by this substitution.

Furthermore, SDS-PAGE was performed in order to investigate whether the phosphorylated STAT3 antibody according to the present invention produced by recombination with the above-described structure (hereinafter referred to as pSTAT3 antibody) produced by expressing it in cells, binds to phosphorylated STAT3. To this end, it was observed whether the antibody binds to target phosphorylated STAT3, by introducing 100 ug of recombinant pSTAT3 antibody into CHO-K1 80M cells and expressed to obtain the corresponding antibody, followed by loading 19.5 ul of each sample in 4-20% acrylamide gel to perform SDS-PAGE.

As a result, as shown in FIG. 2, it was confirmed that all of the pSTAT3 antibody (①-④) samples produced from cells through each independent process effectively bind to pSTAT3.

Example 3. Verification of Cell Penetration Ability of pSTAT3 Bispecific Antibody In order to verify whether the pSTAT3 antibody according to the present invention actually shows a function of penetrating into a cell, a cell penetration capability analysis was performed. To this end, the DLD colorectal cancer cell line was treated with a pSTAT3 bispecific antibody (pSTAT3-C4) containing 3E10 scFv, or a pSTAT3 antibody (STAT3-D31N) containing 3E10 scFv with the 31st aspartic acid substituted into asparagine (D31N). Next, intracellular STAT3 protein was labeled (STAT3 staining) using each pSTAT3 antibody through immunocytochemical staining, and cell nuclei were stained through PI staining (PI staining for nucleus).

As a result, as shown in FIG. 3, when the pSTAT3-D31N antibody was treated, it was observed that the STAT3 staining result was exactly the same as the PI result staining the cell nucleus and, through this, it was confirmed that the antibody penetrates the cell and has the ability to bind to pSTAT3 in the cell. On the other hand, while the STAT3-C4 antibody also showed the ability to penetrate cells and bind to pSTAT3 in the cell, it was found that the cell penetration efficiency was low compared to pSTAT3-D31N.

Example 4. Verification of pSTAT3 Inhibitory Effect of pSTAT3 Bispecific Antibody 4-1. pSTAT3 Inhibitory Effect Verification Through the results of Example 2, it was confirmed that the pSTAT3 antibody of the present invention efficiently binds to pSTAT3. Furthermore, in order to verify the pSTAT3 inhibitory effect of the antibody, Western blot was performed to observe the protein expression level.

Figure 4A:
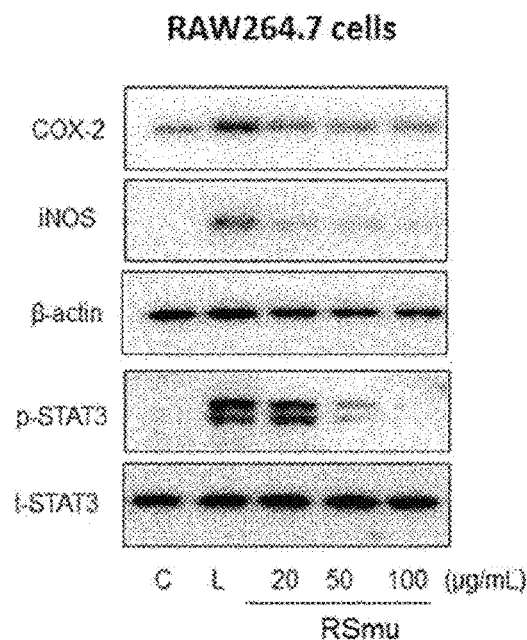
FIG. 4A shows the result in the mouse macrophage cell line (RAW264.7) after inducing STAT3 activity with LPS or TNFα on the expression level of the pSTAT3 protein with the above antibody treatment.
Figure 4B:
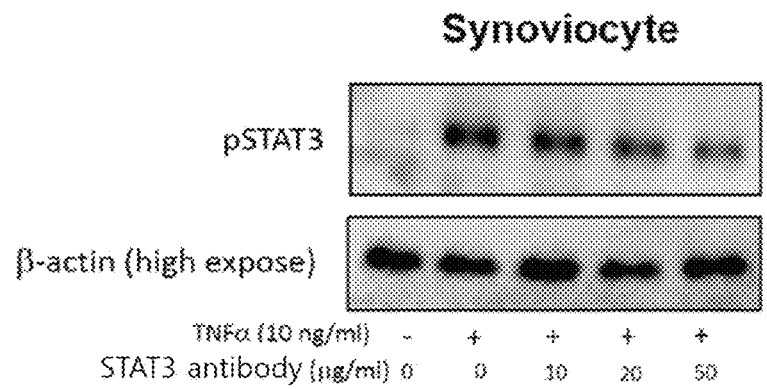
FIG. 4B shows the result in the articular bone marrow cells (Synoviocyte) after inducing STAT3 activity with LPS or TNFα on the expression level of the pSTAT3 protein with the above antibody treatment.

More specifically, the mouse macrophage cell line RAW264.7 and articular bone marrow cells, Synoviocyte, were treated with LPS (lipopolysaccharide) or TNFα to activate pSTAT3, followed by different concentrations of the pSTAT3 antibody of the present invention (20, 50, 100 or 10, 20, 50 ug/ml) and observed the expression level of pSTAT3 protein. As a result, when the pSTAT3 antibody (RSmu) was treated as shown in FIGS. 4A and 4B, it was confirmed that the expression level of pSTAT3 decreased in proportion to the treatment concentration in both cells. Through this, it was found that the pSTAT3 antibody according to the present invention effectively inhibits the pSTAT3 protein activated by LPS or TNFα.

Figure 4C:
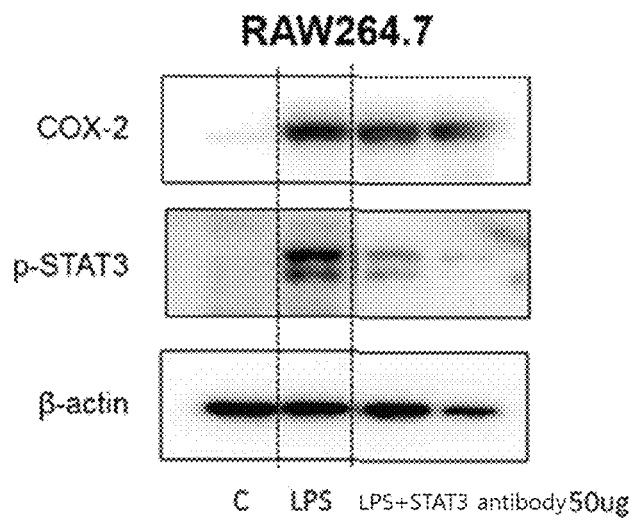
FIG. 4C shows the expression level of pSTAT3 and COX-2 after treating LPS and pSTAT3 in a mouse macrophage cell line. It is the result of confirming the specific binding of the antibody to pSTAT3 according to the present invention.

Furthermore, after treating LPS alone or 50 ug of LPS and pSTAT3 antibody in RAW264.7 cells, the expression level of pSTAT3 and COX-2 induced by NF-κB signaling was observed. As a result, it was confirmed that pSTAT3 antibody of the present invention does not affect the COX-2 protein through the fact that the expression level of COX-2 is not affected while the expression of pSTAT3 protein is decreased as shown in FIG. 4C. These results demonstrate that the antibody selectively inhibits only the activated pSTAT3 protein and does not affect other signaling, thereby demonstrating that side effects can be reduced when using the antibody of the present invention. FIGS. 4A, 4B and 4C are to confirm the pSTAT3 inhibitory ability of the antibody having the pSTAT3 dual specific properties of the present invention.

4-2. Validation of the Inhibitory Effect of pSTAT3 Bispecific Antibodies on STAT3-RE-Mediated Gene Expression.

In addition to the results of Example 4-1, it was intended to verify whether the pSTAT3 antibody of the present invention can inhibit STAT-RE (response element) mediated gene expression by inhibiting the function of STAT3. To this end, a HepG2 hepatocellular carcinoma cell line was transfected with a luciferase reporter gene vector expressed under the control of STAT3-RE for 48 hours, and then treated with the pSTAT3 antibody of the present invention for 1 hour and 100 nM IL-6 was treated for 24 hours. Then, the expression level of STAT3-RE-mediated luciferase gene by IL-6 stimulation was measured.

Figure 5:
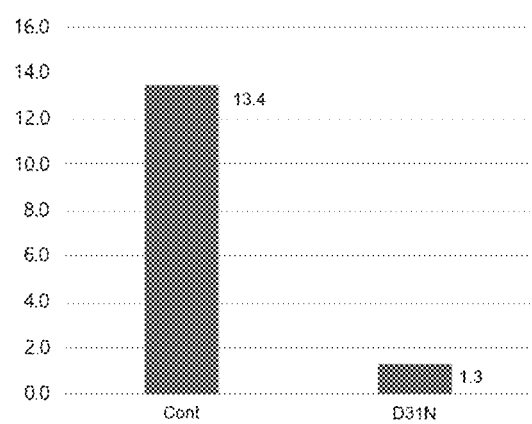
FIG. 5 shows the results in HepG2 liver cancer cells of their response to IL-6 treatment on the level of expression from a luciferase reporter gene under the control of STAT3 responsive element (STAT3-RE) after transient transfection of the reporter gene, and the inhibition of IL-6 induced reporter gene expression by the pretreatment of the cells with a pSTAT3/DNA bispecific antibody provided in the present invention.

As a result, as shown in FIG. 5, when the pSTAT3 antibody (D31N) was treated, it was confirmed that gene expression was almost completely suppressed compared to the control (Cont). From the above results, it was found that the pSTAT3 antibody of the present invention has an effect of inhibiting the expression of the STAT3-mediated gene.

The above description of the present invention is for illustration only, and those skilled in the art to which the present invention pertains can understand that the present invention can be easily modified into other specific forms without changing the technical spirit or essential features of the present invention. Therefore, it should be understood that the embodiments described above are illustrative in all respects and not restrictive.

What is claimed is:

1. A STAT3/DNA bispecific antibody or antigen binding fragment thereof, comprising a first antigen binding site that specifically binds to STAT3 (Signal transducer and activator of transcription 3) and a second antigen-binding site specifically binding to DNA, and thus has a STAT3/DNA bispecific characteristic, wherein, the first antigen-binding site selected from the group consisting of specifically binds to STAT3 with a light chain complementarity determining region (CDR) represented by amino acid sequences of SEQ ID Nos. 1 to 3 and a heavy chain complementarity represented by amino acid sequences of SEQ ID Nos. 4 to 6;

specifically binds to STAT3 with a light chain complementarity determining region (CDR) represented by amino acid sequences of SEQ ID Nos. 7 to 9 and a heavy chain complementarity represented by amino acid sequences of SEQ ID NOs. 10 to 12;

specifically binds to STAT3 with a light chain complementarity determining region (CDR) represented by amino acid sequences of SEQ ID NOs. 13 to 15 and a heavy chain complementarity determining region represented by amino acid sequences of SEQ ID NOs. 16 to 18;

specifically binds to STAT3 with a light chain complementarity determining region (CDR) represented by amino acid sequences of SEQ ID NOs. 19 to 21 and a heavy chain complementarity determining region represented by amino acid sequences of SEQ ID NOs. 22 to 24;

specifically binds to STAT3 with a light chain complementarity determining region (CDR) represented by amino acid sequences of SEQ ID NOs. 25 to 27 and a heavy chain complementarity determining region represented by amino acid sequences of SEQ ID NOs. 28 to 30;

specifically binds to STAT3 with a light chain complementarity determining region (CDR) represented by amino acid sequences of SEQ ID NOs. 31 to 33 and a heavy chain complementarity determining region represented by amino acid sequences of SEQ ID NOs. 34 to 36; and specifically binds to STAT3 with a light chain complementarity determining region (CDR) represented by amino acid sequences of SEQ ID NOs. 37 to 39 and a heavy chain complementarity determining region represented by amino acid sequences of SEQ ID NOs. 40 to 42.

2. The bispecific antibody or antigen binding fragment thereof according to claim 1, wherein the STAT3 is phosphorylated on tyrosine at position 705.

3. The bispecific antibody or antigen binding fragment thereof according to claim 1 characterized by its ability to penetrate into cells.

4. The bispecific antibody or antigen binding fragment thereof according to claim 1, wherein the fragment is selected from a group consisting of diabody, Fab, Fab', F(ab)2, F(ab')2, Fv and scFv.

5. A polynucleotide encoding the bispecific antibody or antigen binding fragment thereof of claim 1.

6. A vector comprising the polynucleotide of claim 5.

7. A cell transformed with the vector of claim 6.

8. A method of producing a STATS/DNA bispecific antibody or antigen binding fragment thereof by:

(a) culturing the cell of claim 7 under conditions in which the polynucleotide is expressed;
(b) producing a polypeptide comprising light and heavy chain variable regions from the cell; and
(c) recovering the polypeptide from the cell or culture medium in which the cell was cultured.

9. A method for detecting a STAT3/DNA bispecific antibody or antigen binding fragment thereof, comprising
contacting the bispecific antibody or fragment thereof of claim 1 with a sample; and
detecting the bispecific antibody or fragment thereof.

10. A pharmaceutical, comprising the bispecific antibody or antigen binding fragment thereof of claim 1 as an active ingredient.

11. A pharmaceutical composition for the treatment of inflammatory diseases, comprising the bispecific antibody or antigen binding fragment thereof of claim 1 as an active ingredient wherein the inflammatory disease is either rheumatoid arthritis or psoriasis dermatitis.

* * * * *

SEQUENCE LISTING

<160> NUMBER OF SEQ ID NOS: 43

<210> SEQ ID NO 1
<211> LENGTH: 13
<212> TYPE: PRT
<213> ORGANISM: Artificial Sequence
<220> FEATURE:
<223> OTHER INFORMATION: pSTAT3 bispecific Ab(C4)_CDR1_Vk

<400> SEQUENCE: 1

Ser Gly Ser Ser Ser Asn Ile Gly Ser Asn His Val Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: pSTAT3 bispecific Ab(C4)_CDR2_Vk

<400> SEQUENCE: 2

Ser Asn Asn Gln Arg Pro Ser
1               5

<210> SEQ ID NO 3
<211> LENGTH: 11
<212> TYPE: PRT
<213> ORGANISM: Artificial Sequence
<220> FEATURE:
<223> OTHER INFORMATION: pSTAT3 bispecific Ab(C4)_CDR3_Vk

<400> SEQUENCE: 3

Ala Ser Trp Asp Tyr Ser Leu Asn Ala Tyr Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: pSTAT3 bispecific Ab(C4)_CDR1_VH

<400> SEQUENCE: 4

Ser Tyr Tyr Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: pSTAT3 bispecific Ab(C4)_CDR2_VH

<400> SEQUENCE: 5

Leu Ile Ser Pro Gly Ser Gly Ser Ile Tyr Tyr Ala Asp Ser Val Lys
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: pSTAT3 bispecific Ab(C4)_CDR3_VH

<400> SEQUENCE: 6

```
Asp Leu Thr Ser Gln Leu Pro Asp Gly Phe Asp Tyr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: pSTAT3 bispecific Ab(3A10)_CDR1_Vk

<400> SEQUENCE: 7

Ser Gly Ser Ser Ser Asn Ile Gly Ser Asn Tyr Val Ser
1               5                   10

<210> SEQ ID NO 8
<211> LENGTH: 7
<212> TYPE: PRT
<213> ORGANISM: Artificial Sequence
<220> FEATURE:
<223> OTHER INFORMATION: pSTAT3 bispecific Ab(3A10)_CDR2_Vk

<400> SEQUENCE: 8

Ser Asn Asn Gln Arg Pro Ser
1               5

<210> SEQ ID NO 9
<211> LENGTH: 11
<212> TYPE: PRT
<213> ORGANISM: Artificial Sequence
<220> FEATURE:
<223> OTHER INFORMATION: pSTAT3 bispecific Ab(3A10)_CDR3_Vk

<400> SEQUENCE: 9

Gly Thr Trp Asp Tyr Ser Leu Ser Gly Tyr Val
1               5                   10

<210> SEQ ID NO 10
<211> LENGTH: 5
<212> TYPE: PRT
<213> ORGANISM: Artificial Sequence
<220> FEATURE:
<223> OTHER INFORMATION: pSTAT3 bispecific Ab(3A10)_CDR1_VH

<400> SEQUENCE: 10

Asn Tyr Ala Met Ser
1               5

<210> SEQ ID NO 11
<211> LENGTH: 17
<212> TYPE: PRT
<213> ORGANISM: Artificial Sequence
<220> FEATURE:
<223> OTHER INFORMATION: pSTAT3 bispecific Ab(3A10)_CDR2_VH

<400> SEQUENCE: 11

Gly Ile Ser His Asp Asp Gly Ser Lys Tyr Tyr Ala Asp Ser Val Lys
1               5                   10                  15
Gly

<210> SEQ ID NO 12
<211> LENGTH: 18
<212> TYPE: PRT
<213> ORGANISM: Artificial Sequence
<220> FEATURE:
<223> OTHER INFORMATION: pSTAT3 bispecific Ab(3A10)_CDR3_VH

<400> SEQUENCE: 12
```

```
Gly Gly Ile Ser Cys Ser Arg Thr Gly Cys Tyr Ser Ala Asp Ala Met
1               5                   10                  15

Asp Val

<210> SEQ ID NO 13
<211> LENGTH: 13
<212> TYPE: PRT
<213> ORGANISM: Artificial Sequence
<220> FEATURE:
<223> OTHER INFORMATION: pSTAT3 bispecific Ab(C6)_CDR1_Vk

<400> SEQUENCE: 13

Thr Gly Ser Ser Ser Asn Ile Gly Asn Asn Tyr Val Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: pSTAT3 bispecific Ab(C6)_CDR2_Vk

<400> SEQUENCE: 14

Tyr Asp Ser Lys Arg Pro Ser
1               5

<210> SEQ ID NO 15
<211> LENGTH: 11
<212> TYPE: PRT
<213> ORGANISM: Artificial Sequence
<220> FEATURE:
<223> OTHER INFORMATION: pSTAT3 bispecific Ab(C6)_CDR3_Vk

<400> SEQUENCE: 15

Gly Ser Trp Asp Ala Ser Leu Asn Gly Tyr Val
1               5                   10

<210> SEQ ID NO 16
<211> LENGTH: 5
<212> TYPE: PRT
<213> ORGANISM: Artificial Sequence
<220> FEATURE:
<223> OTHER INFORMATION: pSTAT3 bispecific Ab(C6)_CDR1_VH

<400> SEQUENCE: 16

Asp Tyr Ala Met Ser
1               5

<210> SEQ ID NO 17
<211> LENGTH: 17
<212> TYPE: PRT
<213> ORGANISM: Artificial Sequence
<220> FEATURE:
<223> OTHER INFORMATION: pSTAT3 bispecific Ab(C6)_CDR2_VH

<400> SEQUENCE: 17

Gly Ile Ser Ser Ser Gly Gly Ser Lys Tyr Tyr Ala Asp Ser Val Lys
1               5                   10                  15

Gly

<210> SEQ ID NO 18
<211> LENGTH: 18
<212> TYPE: PRT
<213> ORGANISM: Artificial Sequence
<220> FEATURE:
```

```
<223> OTHER INFORMATION: pSTAT3 bispecific Ab(C6)_CDR3_VH

<400> SEQUENCE: 18

Phe Arg Arg Thr His Ser Thr Arg Asn Thr Ser Tyr Tyr Asn Gly Met
1               5                   10                  15
Asp Val

<210> SEQ ID NO 19
<211> LENGTH: 13
<212> TYPE: PRT
<213> ORGANISM: Artificial Sequence
<220> FEATURE:
<223> OTHER INFORMATION: pSTAT3 bispecific Ab(H9)_CDR1_Vk

<400> SEQUENCE: 19

Ser Gly Ser Ser Ser Asn Ile Gly Ser Asn Tyr Val Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: pSTAT3 bispecific Ab(H9)_CDR2_Vk

<400> SEQUENCE: 20

Asp Asn Ser Gln Arg Pro Ser
1               5

<210> SEQ ID NO 21
<211> LENGTH: 11
<212> TYPE: PRT
<213> ORGANISM: Artificial Sequence
<220> FEATURE:
<223> OTHER INFORMATION: pSTAT3 bispecific Ab(H9)_CDR3_Vk

<400> SEQUENCE: 21

Ala Thr Trp Asp Asp Ser Leu Asn Gly Tyr Val
1               5                   10

<210> SEQ ID NO 22
<211> LENGTH: 5
<212> TYPE: PRT
<213> ORGANISM: Artificial Sequence
<220> FEATURE:
<223> OTHER INFORMATION: pSTAT3 bispecific Ab(H9)_CDR1_VH

<400> SEQUENCE: 22

Ser Tyr Asp Met Ser
1               5

<210> SEQ ID NO 23
<211> LENGTH: 17
<212> TYPE: PRT
<213> ORGANISM: Artificial Sequence
<220> FEATURE:
<223> OTHER INFORMATION: pSTAT3 bispecific Ab(H9)_CDR2_VH

<400> SEQUENCE: 23

Val Ile Ser Pro Gly Ser Gly Ser Lys Tyr Tyr Ala Asp Ser Val Arg
1               5                   10                  15
Gly

<210> SEQ ID NO 24
<211> LENGTH: 7
```

```
<212> TYPE: PRT
<213> ORGANISM: Artificial Sequence
<220> FEATURE:
<223> OTHER INFORMATION: pSTAT3 bispecific Ab(H9)_CDR3_VH

<400> SEQUENCE: 24

Ser Trp Gln Lys Phe Asp Tyr
1               5

<210> SEQ ID NO 25
<211> LENGTH: 13
<212> TYPE: PRT
<213> ORGANISM: Artificial Sequence
<220> FEATURE:
<223> OTHER INFORMATION: pSTAT3 bispecific Ab(A12)_CDR1_Vk

<400> SEQUENCE: 25

Ser Arg Ser Ser Ser Asn Ile Gly Ser Asn Ser Val Thr
1               5                   10

<210> SEQ ID NO 26
<211> LENGTH: 7
<212> TYPE: PRT
<213> ORGANISM: Artificial Sequence
<220> FEATURE:
<223> OTHER INFORMATION: pSTAT3 bispecific Ab(A12)_CDR2_Vk

<400> SEQUENCE: 26

Ser Asn Ser Gln Arg Pro Ser
1               5

<210> SEQ ID NO 27
<211> LENGTH: 11
<212> TYPE: PRT
<213> ORGANISM: Artificial Sequence
<220> FEATURE:
<223> OTHER INFORMATION: pSTAT3 bispecific Ab(A12)_CDR3_Vk

<400> SEQUENCE: 27

Ala Ser Trp Asp Asp Ser Leu Asn Gly Tyr Val
1               5                   10

<210> SEQ ID NO 28
<211> LENGTH: 5
<212> TYPE: PRT
<213> ORGANISM: Artificial Sequence
<220> FEATURE:
<223> OTHER INFORMATION: pSTAT3 bispecific Ab(A12)_CDR1_VH

<400> SEQUENCE: 28

Asn Tyr Ala Met Ser
1               5

<210> SEQ ID NO 29
<211> LENGTH: 17
<212> TYPE: PRT
<213> ORGANISM: Artificial Sequence
<220> FEATURE:
<223> OTHER INFORMATION: pSTAT3 bispecific Ab(A12)_CDR2_VH

<400> SEQUENCE: 29

Ser Ile Ser Pro Gly Asn Gly Ser Ile Tyr Tyr Ala Asp Ser Val Lys
1               5                   10                  15
Gly

<210> SEQ ID NO 30
```

```
<211> LENGTH: 18
<212> TYPE: PRT
<213> ORGANISM: Artificial Sequence
<220> FEATURE:
<223> OTHER INFORMATION: pSTAT3 bispecific Ab(A12)_CDR3_VH

<400> SEQUENCE: 30

Ala Pro Arg His Cys Ser Met His Leu Cys Tyr Ser Ser Asn Ala Met
1               5                   10                  15

Asp Val

<210> SEQ ID NO 31
<211> LENGTH: 13
<212> TYPE: PRT
<213> ORGANISM: Artificial Sequence
<220> FEATURE:
<223> OTHER INFORMATION: pSTAT3 bispecific Ab(F11)_CDR1_Vk

<400> SEQUENCE: 31

Thr Gly Ser Ser Ser Asn Ile Gly Asn Asn Ser Val Ser
1               5                   10

<210> SEQ ID NO 32
<211> LENGTH: 7
<212> TYPE: PRT
<213> ORGANISM: Artificial Sequence
<220> FEATURE:
<223> OTHER INFORMATION: pSTAT3 bispecific Ab(F11)_CDR2_Vk

<400> SEQUENCE: 32

Ser Asp Ser Lys Arg Pro Ser
1               5

<210> SEQ ID NO 33
<211> LENGTH: 11
<212> TYPE: PRT
<213> ORGANISM: Artificial Sequence
<220> FEATURE:
<223> OTHER INFORMATION: pSTAT3 bispecific Ab(F11)_CDR3_Vk

<400> SEQUENCE: 33

Gly Thr Trp Asp Asp Ser Leu Ser Gly Tyr Val
1               5                   10

<210> SEQ ID NO 34
<211> LENGTH: 5
<212> TYPE: PRT
<213> ORGANISM: Artificial Sequence
<220> FEATURE:
<223> OTHER INFORMATION: pSTAT3 bispecific Ab(F11)_CDR1_VH

<400> SEQUENCE: 34

Gly Tyr Asp Met Ser
1               5

<210> SEQ ID NO 35
<211> LENGTH: 17
<212> TYPE: PRT
<213> ORGANISM: Artificial Sequence
<220> FEATURE:
<223> OTHER INFORMATION: pSTAT3 bispecific Ab(F11)_CDR2_VH

<400> SEQUENCE: 35

Val Ile Ser Pro Gly Ser Gly Ser Lys Tyr Tyr Ala Asp Ser Val Arg
1               5                   10                  15

Gly
```

<210> SEQ ID NO 36
<211> LENGTH: 7
<212> TYPE: PRT
<213> ORGANISM: Artificial Sequence
<220> FEATURE:
<223> OTHER INFORMATION: pSTAT3 bispecific Ab(F11)_CDR3_VH

<400> SEQUENCE: 36

Ser Phe Arg Thr Phe Asp Tyr
1               5

<210> SEQ ID NO 37
<211> LENGTH: 13
<212> TYPE: PRT
<213> ORGANISM: Artificial Sequence
<220> FEATURE:
<223> OTHER INFORMATION: pSTAT3 bispecific Ab(A10)_CDR1_Vk

<400> SEQUENCE: 37

Thr Gly Ser Ser Ser Asn Ile Gly Asn Asn Tyr Val Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: pSTAT3 bispecific Ab(A10)_CDR2_Vk

<400> SEQUENCE: 38

Ala Asp Ser Lys Arg Pro Ser
1               5

<210> SEQ ID NO 39
<211> LENGTH: 11
<212> TYPE: PRT
<213> ORGANISM: Artificial Sequence
<220> FEATURE:
<223> OTHER INFORMATION: pSTAT3 bispecific Ab(A10)_CDR3_Vk

<400> SEQUENCE: 39

Gly Ala Trp Asp Ser Ser Leu Ser Gly Tyr Val
1               5                   10

<210> SEQ ID NO 40
<211> LENGTH: 5
<212> TYPE: PRT
<213> ORGANISM: Artificial Sequence
<220> FEATURE:
<223> OTHER INFORMATION: pSTAT3 bispecific Ab(A10)_CDR1_VH

<400> SEQUENCE: 40

Asp Tyr Ala Met Ser
1               5

<210> SEQ ID NO 41
<211> LENGTH: 17
<212> TYPE: PRT
<213> ORGANISM: Artificial Sequence
<220> FEATURE:
<223> OTHER INFORMATION: pSTAT3 bispecific Ab(A10)_CDR2_VH

<400> SEQUENCE: 41

Trp Ile Ser Pro Gly Gly Ser Ser Ile Tyr Tyr Ala Asp Ser Val Lys
1               5                   10                  15

Gly

<210> SEQ ID NO 42
<211> LENGTH: 12
<212> TYPE: PRT
<213> ORGANISM: Artificial Sequence
<220> FEATURE:
<223> OTHER INFORMATION: pSTAT3 bispecific Ab(A10)_CDR3_VH

<400> SEQUENCE: 42

Gly Gly Arg Ala Tyr Arg Val Pro Ala Phe Asp Tyr
1               5                   10

<210> SEQ ID NO 43
<211> LENGTH: 547
<212> TYPE: PRT
<213> ORGANISM: Artificial Sequence
<220> FEATURE:
<223> OTHER INFORMATION: pSTAT3 antibody

<400> SEQUENCE: 43

Met Gly Phe Ser Arg Ile Phe Leu Phe Leu Leu Ser Val Thr Thr Gly
1               5                   10                  15

Val His Ser Asp Ile Val Leu Thr Gln Ser Pro Ala Ser Leu Ala Val
            20                  25                  30

Ser Leu Gly Gln Arg Ala Thr Ile Ser Cys Arg Ala Ser Lys Ser Val
        35                  40                  45

Ser Thr Ser Ser Tyr Ser Tyr Met His Trp Tyr Gln Gln Lys Pro Gly
    50                  55                  60

Gln Pro Pro Lys Leu Leu Ile Lys Tyr Ala Ser Tyr Leu Glu Ser Gly
65                  70                  75                  80

Val Pro Ala Arg Phe Ser Gly Ser Gly Ser Gly Thr Asp Phe Thr Leu
                85                  90                  95

Asn Ile His Pro Val Glu Glu Glu Asp Ala Ala Thr Tyr Tyr Cys Gln
            100                 105                 110

Gln Ser Arg Glu Phe Pro Trp Thr Phe Gly Gly Gly Thr Lys Leu Glu
        115                 120                 125

Leu Lys Gly Gly Gly Gly Ser Gly Gly Gly Gly Ser Gly Gly Gly Gly
    130                 135                 140

Ser Glu Val Gln Leu Val Glu Ser Gly Gly Leu Val Lys Pro Gly Gly
145                 150                 155                 160

Gly Ser Arg Lys Leu Ser Cys Ala Ala Ser Gly Phe Thr Phe Ser Asp
                165                 170                 175

Tyr Gly Met His Trp Val Arg Gln Ala Pro Glu Lys Gly Leu Glu Trp
            180                 185                 190

Val Ala Tyr Ile Ser Ser Gly Ser Ser Thr Ile Tyr Tyr Ala Asp Thr
        195                 200                 205

Val Lys Gly Arg Phe Thr Ile Ser Arg Asp Asn Ala Lys Asn Thr Leu
    210                 215                 220

Phe Leu Gln Met Thr Ser Leu Arg Ser Glu Asp Thr Ala Met Tyr Tyr
225                 230                 235                 240

Cys Ala Arg Arg Gly Leu Leu Leu Asp Tyr Trp Gly Gln Gly Thr Thr
                245                 250                 255

Leu Thr Val Ser Ser Glu Gln Lys Leu Ile Ser Glu Glu Asp Leu Ala
            260                 265                 270

Lys Thr Thr Ala Pro Ser Val Tyr Pro Leu Ala Pro Val Leu Glu Ser
        275                 280                 285

```
Ser Gly Ser Gly Gln Ser Val Leu Thr Gln Pro Pro Ser Ala Ser Gly
    290                 295                 300

Thr Pro Gly Gln Arg Val Thr Ile Ser Cys Ser Gly Ser Ser Ser Asn
305             310                 315                     320

Ile Gly Ser Asn His Val Ser Trp Tyr Gln Gln Leu Pro Gly Thr Ala
                325                 330                 335

Pro Lys Leu Leu Ile Tyr Ser Asn Asn Gln Arg Pro Ser Gly Val Pro
                340                 345                 350

Asp Arg Phe Ser Gly Ser Lys Ser Gly Thr Ser Ala Ser Leu Ala Ile
            355                 360                 365

Ser Gly Leu Arg Ser Glu Asp Glu Ala Asp Tyr Tyr Cys Ala Ser Trp
    370                 375                 380

Asp Tyr Ser Leu Asn Ala Tyr Val Phe Gly Gly Gly Thr Lys Leu Thr
385             390                 395                     400

Val Leu Gly Gln Ala Gly Gly Gly Ser Gly Gly Gly Gly Ser Gly
                405                 410                 415

Gly Gly Gly Ser Glu Val Gln Leu Leu Glu Ser Gly Gly Gly Leu Val
                420                 425                 430

Gln Pro Gly Gly Ser Leu Arg Leu Ser Cys Ala Val Ser Gly Phe Thr
        435                 440                 445

Phe Ser Ser Tyr Tyr Met Ser Trp Val Arg Gln Ala Pro Gly Lys Gly
    450                 455                 460

Leu Glu Trp Val Ser Leu Ile Ser Pro Gly Ser Gly Ser Ile Tyr Tyr
465             470                 475                     480

Ala Asp Ser Val Lys Gly Arg Phe Thr Ile Ser Arg Asp Asn Ser Lys
                485                 490                 495

Asn Thr Leu Tyr Leu Gln Met Asn Ser Leu Arg Ala Glu Asp Thr Ala
            500                 505                 510

Val Tyr Tyr Cys Ala Arg Asp Leu Thr Ser Gln Leu Pro Asp Gly Phe
            515                 520                 525

Asp Tyr Trp Gly Gln Gly Thr Leu Val Thr Val Ser Ser His His His
    530                 535                 540

His His His
545
```